United States Patent
Delee et al.

(10) Patent No.: US 6,881,258 B2
(45) Date of Patent: Apr. 19, 2005

(54) MIXTURE FOR THE PRODUCTION OF A HIGH-EXPANSION STONE DIE

(75) Inventors: Paul Delee, Leuven (BE); Haruhiko Horiuchi, Leuven (BE)

(73) Assignee: GC Europe N.V., Leuven (BE)

( * ) Notice: Subject to any disclaimer, the term of this patent is extended or adjusted under 35 U.S.C. 154(b) by 0 days.

(21) Appl. No.: 10/419,664

(22) Filed: Apr. 21, 2003

(65) Prior Publication Data

US 2004/0031421 A1 Feb. 19, 2004

(30) Foreign Application Priority Data

May 10, 2002 (EP) ............................................. 02010127

(51) Int. Cl.⁷ ......................... C04B 28/14; C04B 11/00; A61K 6/02; A61K 6/00
(52) U.S. Cl. ...................... 106/788; 106/35; 106/38.35; 106/772; 106/781; 264/333
(58) Field of Search ................................ 106/35, 38.35, 106/772, 781, 788, 778; 264/333

(56) References Cited

U.S. PATENT DOCUMENTS

| | | |
|---|---|---|
| 2,639,478 A | 5/1953 | Duffy et al. |
| 4,526,619 A | 7/1985 | Ohi et al. |
| 4,604,142 A | 8/1986 | Kamohara et al. |
| 4,647,311 A | 3/1987 | Ohi et al. |
| 4,909,847 A | 3/1990 | Ohi et al. |
| 4,911,759 A | 3/1990 | Ohi et al. |

FOREIGN PATENT DOCUMENTS

| | | |
|---|---|---|
| DE | 27 40 018 | 3/1979 |
| DE | 195 48 655 | 6/1997 |
| EP | 1 186 577 | 3/2002 |

*Primary Examiner*—Anthony J. Green
(74) *Attorney, Agent, or Firm*—Frommer Lawrence & Haug LLP; Ronald R. Santucci

(57) ABSTRACT

The present invention refers to a mixture comprising alpha $CaSO_4 \times \frac{1}{2} H_2O$, $CaSO_4 \times 2 H_2O$, a combination of a hardening accelerator, a hardening retarder and a setting expansion inhibitor, and optionally a surfactant.

The mixture can be used to prepare a die having an extremely high setting expansion.

8 Claims, No Drawings

MIXTURE FOR THE PRODUCTION OF A HIGH-EXPANSION STONE DIE

The present invention relates to a mixture for the production of a die.

In recent times dental implants, bridges and crowns were prepared using gold since gold has superior properties and can be processed quite easily. Today, people require ceramic materials for aesthetic reasons. However, processing of ceramic material is quite complex and requires a lot of time and work so that new improved techniques are needed to process ceramic materials more effectively.

When producing ceramic implants, crowns or bridges, a model (master model) of the tooth to be covered with the ceramic material is prepared. Then the master model is duplicated with a die material like gypsum or plaster as disclosed in the book "Gips . . . und was man darüber wissen sollte" (Martin Kuske & Ralf Suckert—teamwork media—2000) especially chapter 1, page 18 ff. Known dental plasters are divided according to the norm DIN/EN 26873 IS 6873 into five types:

| Type | Setting Expansion % | Compression strength in Mpa min | max |
|---|---|---|---|
| I | 0 to 0.15 | 4 | 4 |
| II | 0 to 0.30 | 9 | — |
| III | 0 to 0.20 | 20 | — |
| IV | 0 to 0.15 | 35 | — |
| V | 0.16 to 0.30 | 35 | — |

Such plasters have a setting expansion of at most 0, 3%. The die, produced with this kind of plaster, is covered with a ceramic suspension to build a ceramic cap (also called green body before the sintering process) and then the covered die is dried at temperatures of about 900° C. In a second step, die and cap are separated and the ceramic cap is heated (sintered) to about 1400 to 1500° C. At such temperatures the ceramic material of the cap shrinks to an extent of from about 4% up to 12%. Accordingly, the cap is too small and does not fit on the patient's tooth so that the ceramic cap has to be adapted to the tooth by removing ceramic material. Repeatedly, the fit of the cap on the tooth is tested and excess material removed until a good fit has been achieved. This procedure is time-consuming, expensive and inconvenient for the patient.

In order to overcome this disadvantage it has been proposed to provide a die material which expands during setting. If such material is used, the die material and accordingly the ceramic material covering the die would have a too big/loose fit in a pre-sintered stage so that a good fit of the final sintered ceramic cap to the tooth would be achieved. However, no such material is available: As mentioned above, currently available plaster has a setting expansion of up to 0.3% which is far from satisfactory.

It was accordingly an object of the present invention to provide a material which overcomes this disadvantage of the prior art.

It was especially an object of the present invention to provide a die material which expands to an extent that the shrinkage of a ceramic cap can be neutralized. Thus, a die which consists of such material can be used for the production of a ceramic cap which needs no further modification and fits exactly onto a patient's tooth.

This object has been achieved according to the present invention by providing a mixture, comprising:

a) 100 parts by weight α $CaSO_4 \times \frac{1}{2} H_2O$,
b) 1–20 parts by weight $CaSO_4 \times 2 H_2O$,
c) 0.005–0.80 parts by weight of at least one additive and
d) up to 2 parts by weight of one or more surfactants.

This mixture can further comprise:

e) 15–65, preferably 23–45 parts by weight of a liquid such as water or a colloidal silica suspension.

The mixtures according to the present invention can be used to prepare a die which has a setting expansion of about 4 to about 14%. When such a die is covered with a ceramic material and heated to, e.g., about 900° C., the die and accordingly the ceramic material expand to a corresponding degree. When the ceramic cap is then removed from the die and fired at a temperature of, e.g. 1400° C. to 1500° C. the ceramic material shrinks to its original size so that the cap fits exactly to the patients tooth.

Some or all components a), b), c) and optionally d) and/or e) will usually be provided in separate containers as a kit of parts so that the dentist or the dental laboratory can combine them in any appropriate ratio. It is also possible to provide a mixture of components a)–c) and optionally d) with a defined expansion ratio. This mixture can be mixed with water in a recommended ratio. Alternatively component e) can be provided in a predetermined amount, again resulting in a specific expansion of the die when all components are mixed.

According to one embodiment of the present invention, a die can be produced by mixing components a) to c) and e) and optionally one or more of components d), preferably while stirring the mixture. According to this embodiment, the material is then poured into a mold which is an exact negative of the patient's tooth to be treated. Care should be taken at this stage to avoid voids in the die; if voids are formed at a surface of the die, protrusions will be formed on the cap which will have to be removed during further work-up. If voids are formed within the die, the die will not be homogenous thereby preventing a linear expansion of the die. This also results in a cap which must be worked-up with considerable difficulty. Methods to prevent formations of voids in a die are known in the art and should accordingly be applied in the present case.

When the die has hardened to a degree that it can be handled without being damaged, it is covered with a ceramic cap e.g. by dipping the die into ceramic material, drying the ceramic material and repeating these steps until the required strength and size of the ceramic cap has been achieved. The materials are then heated to a temperature of e.g. about 900° C. During this heating step, the die expands to the required degree, thereby co-expanding the ceramic cap. The cap is then removed from the die and heated to a temperature of about 1400 to about 1500° C. During this sintering step, the cap shrinks depending upon the ceramic material used, e.g. by about 13%, thereby regaining the required size.

A further advantage of the present invention is that the properties, especially the expansion of the die can be varied to a large extent: If the ceramic material used for the production of a cap has a specific shrinkage, the mixture according to the present invention can be adapted so that the die expands to exactly meet this shrinkage.

There are a number of factors which influence the properties such as setting and thermal expansion and compressive strength of the die. All solid materials used in the present invention are preferably employed as powders or fine grains. They can e.g. have an average particle size of about 3 $\mu m$ to about 70 $\mu m$.

1. The Type of the α $CaSO_4 \times \frac{1}{2} H_2O$ a)

An important factor is the quality and type of the α $CaSO_4 \times \frac{1}{2} H_2O$ to be used. Basically any a gypsum hemihydrate or any mixture thereof can be used. Examples are synthetic gypsum T, natural gypsum K and natural gypsum PL, all of which are commercially available. If synthetic gypsum T is used, the expansion of the resulting die is larger than when natural gypsum K or natural gypsum PL are used, please compare with Table 1.

2. The Amount and the Type of the $CaSO_4 \times 2\ H_2O$ b)

A further important factor is the quality and type of the dihydrate to be used. Basically any dihydrate and any commercially available dihydrate can be used.

Moreover, the amount of the dihydrate to be added to the mixture has a large influence on the properties of the resulting die. As can be taken from table 2 an increase from 2 parts by weight to 10 parts by weight increases the expansion from 3–4% to 11–12%. The dihydrate can be used in amounts of about 1–20 parts by weight, while 2–15 parts by weight are preferred. As mentioned above, the amount will be determined depending on the requested properties of the die.

3. The Amount and the Type of Additives c)

The mixture according to the present invention can comprise one, two or more additives. Examples of such additives are hardening accelerators, hardening retarders, and setting expansion inhibitors. Such components are described in e.g. Skinner's Science of Dental Materials, Ralph W. Phillips, 1982, 8$^{th}$ edition.

For example, as the hardening retarder(s), carboxylates (citrate, succinate, . . . etc) and water soluble high polymers (cane sugar, hexameta phosphate, . . . etc) can be used in the present invention. Preferably tri sodium citrate is used.

For example, as the hardening accelerator(s) inorganic acid salts (sodium chloride, potassium sulfate, . . . etc) may be used in the present invention. Preferably potassium sulfate is used.

For example, as the setting expansion inhibitor potassium salts and sodium salts etc. (potassium chloride, potassium tartrate, potassium sodium, sodium tartrate, . . . etc) can be used in the present invention. Preferably potassium tartrate is used.

Depending on the amount and combination of the additives, the physical properties such as setting time, setting expansion and compressive strength of the die can be varied, please refer to table 2. The amount of these additives can vary from 0.005 to 0.8 parts by weight, whereas a range of 0.01 to 0.4 parts by weight is preferred. One or a mixture of two or more additives can be used.

4. The Amount and the Type of Surfactant d)

Especially a water reducing agent and/or dispersing agent can be used as a surfactant. Such agents are, for example,
   anionic surfactants like alkylbenzene sulfonate, alkylnaphthalene sulfonate,
   a mixture of naphtalene sulfonates and formaldehyde polycondensation products,
   a mixture of melamin sulfonates and formaldehyde polycondensation products, dialkyl sulfosuccinates, alkylsulfonates,
   alpha-olefin sulfonates, sodium N-acyl methyl taurate,
   nonionic surfactants like polyethylene alkylether, polyoxyethylene sec-alcohol ether,
   polyethylene polyoxypropylene alkylether,
   polyglyceryl fatty acid ester.

An especially preferred surfactant is a mixture of melamin sulfonates and formaldehyd polycondensation products.

One function of the surfactant is to reduce the amount of liquid required for mixing and to increase the setting expansion. Commercially available surfactants are e.g. Pozzolith NR. 70, NR. 81 MP, NR. NL-1440 or NR. NL-4000.

The surfactants can be used in amounts of up to 2 parts by weight, while amounts of 0.2 to 1 parts by weight are preferred. It is, however, possible to omit the surfactants altogether. Moreover, one or a mixture of two or more surfactants can be used.

5. The Amount and the Type of the Liquid e) to be Used

The liquid(s) which can be used also can have an important influence on the properties and especially the setting expansion of the die. Preferably, a colloidal silica suspension is used. Commercially available examples are e.g. Levasil (Bayer) 100/45%, 200/40%, LUDOX (Dupont) H540, W30, W50. The colloidal silica suspension is usually diluted to a concentration of about 20 to 50 weight-% using distilled or tap water. Alternatively, distilled or tap water can be used as the liquid. Preferred amounts of the liquid to be added to the mixture of components a)–c) and optionally component(s) d) are 23 to 45 g liquid per 100 g of the mixture.

Thus, by varying the quality and/or the quantity of the above components, the properties and especially the expansion of the die can be adapted. For example, the shrinkage of a desired ceramic material can be determined and then a specific die can be selected based on the teaching of the present invention which has the appropriate shrinkage.

The present invention furthermore discloses a kit of parts especially for dental purposes, containing at least components a), b) and c) preferably each in separate containers. Additionally it can contain component(s) d), also in (a) separate container(s).

The components can be provided in pre-determined quantities and qualities so that a die material with specific properties such as expansion etc. can be prepared in a dental laboratory by the dentist or technician.

EXAMPLES

Examples of compositions of the present invention are described in the following tables.

(Instruction for Use)

Powder (components a), b), c) and optionally d))/Liquid ratio:

about 100 g/23 g–45 g

Hand mix powder into liquid for 15 seconds.

Blend to a homogenous mixture.

Pour into mold, especially a duplicate impression.

Bench setting for 10 minutes.

After 10 minutes remove from impression and put into water for total setting time (EX 2 hours) to get available setting expansion.

TABLE 1

The difference of α $CaSO_4\ 1/2H_2O$

| (Composition) | EX 1 (Weight ratio) | EX 2 (Weight ratio) | EX 3 (Weight ratio) |
| --- | --- | --- | --- |
| α $CaSO_4\ 1/2H_2O$ | Synthetic gypsum T | Natural gypsum K | Natural gypsum PL |
| | 100 | 100 | 100 |
| $CaSO_4\ 2H_2O$ | 10 | 10 | 10 |
| Surfactant: a mixture of melaminsulfonate and a formaldehyde polycondensation product | 0.2 | 0.2 | 0.2 |
| Hardening retarder: tri sodium citrate | 0.1 | 0.1 | 0.1 |
| Hardening accelerator: potassium sulfate | 0 | 0 | 0 |

TABLE 1-continued

The difference of α CaSO₄ 1/2H₂O

| (Composition) | EX 1 (Weight ratio) | EX 2 (Weight ratio) | EX 3 (Weight ratio) |
|---|---|---|---|
| Setting expansion inhibitor: potassium tartrate | 0 | 0 | 0 |
| (Physical properties) | | | |
| Liquid concentration | 40% | 40% | 40% |
| Liquid / Powder ratio | 28 g/100 g | 31 g/100 g | 32 g/100 g |
| Setting time (ISO) | 8'00" | 10'00" | 11'00" |
| Setting     Iso/2 hrs | More | More | More |

TABLE 1-continued

The difference of α CaSO₄ 1/2H₂O

| (Composition) | | EX 1 (Weight ratio) | EX 2 (Weight ratio) | EX 3 (Weight ratio) |
|---|---|---|---|---|
| expansion | | than 4% | than 3% | than 3% |
| | In water/2 hrs | 11.0~11.5% | 7.0~7.5% | 7.0~7.5% |
| Compressive | ISO/1 hr | 50 Mpa | 50 Mpa | 50 Mpa |
| strength | In water/2 hrs | 30 Mpa | 30 Mpa | 30 Mpa |

TABLE 2

The difference of additives(1)

| (Composition) | EX 1 (Weight ratio) | EX 2 (Weight ratio) | EX 3 (Weight ratio) | EX 4 (Weight ratio) | EX 5 (Weight ratio) | EX 6 (Weight ratio) |
|---|---|---|---|---|---|---|
| α CaSO₄ 1/2H₂O | 100 | 100 | 100 | 100 | 100 | 100 |
| CaSO₄ 2H₂O | 2 | 10 | 15 | 10 | 10 | 10 |
| Surfactant: a mixture of melaminsulfonate and a formaldehyde polycondensation product | 0.2 | 0.2 | 0.2 | 0 | 1.0 | 2.0 |
| Hardening retarder: tri sodium citrate | 0.005~0.05 | 0.06~0.10 | 0.10~0.20 | 0.06~0.10 | 0.06~0.10 | 0.06~0.10 |
| Hardening accelerator: potassium sulfate | 0 | 0 | 0 | 0 | 0 | 0 |
| Setting expansion inhibitor: potassium tartrate | 0 | 0 | 0 | 0 | 0 | 0 |
| (Physical properties) | 0 | 0 | 0 | 0 | 0 | 0 |
| Liquid concentration | 40% | 40% | 40% | 40% | 40% | 40% |
| Liquid/Powder ratio | 28 g/100 g | 28 g/100 g | 28 g/100 g | 28 g/100 g | 28 g/100 g | 28 g/100 g |
| Setting time (ISO) | 3'00"~10'00" | 5'00"~10'00" | 5'00"~10'00" | 6'00"~11'00" | 5'00"~10'00" | 2'30"~5'00" |
| Setting       Iso/2 hrs | — | — | — | — | — | — |
| expansion    In water/2 hrs | 3%~4% | 11%~12% | 10%~11% | 10%~11% | 11%~12% | 12%~13% |
| Com-         ISO/1 hr | 50 Mpa | 50 Mpa | 50 Mpa | 50 Mpa | 50 Mpa | 50 Mpa |
| pressive     In water/2 hrs | 30 Mpa | 30 Mpa | 30 Mpa | 30 Mpa | 30 Mpa | 30 Mpa |
| strength | | | | | | |

TABLE 3

The difference of additives(2)

| (Composition) | EX 1 (Weight ratio) | EX 2 (Weight ratio) | EX 3 (Weight ratio) | EX 4 (Weight ratio) | EX 5 (Weight ratio) | EX 6 (Weight ratio) |
|---|---|---|---|---|---|---|
| α CaSO₄ 1/2H₂O | 100 | 100 | 100 | 100 | 100 | 100 |
| CaSO₄ 2H₂O | 10 | 10 | 10 | 10 | 10 | 10 |
| Surfactant: a mixture of melaminsulfonate and a formaldehyde polycondensation product | 0.2 | 0.2 | 0.2 | 0.2 | 0.2 | 0.2 |
| Hardening retarder: tri sodium citrate | 0.06~0.10 | 0.06~0.10 | 0.06~0.10 | 0.06~0.10 | 0.06~0.10 | 0.10~0.40 |
| Hardening accelerator: potassium sulfate | 0 | 0.1 | 0.2 | 0 | 0 | 0.2 |
| Setting expansion inhibitor: potassium tartrate | 0 | 0 | 0 | 0.1 | 0.2 | 0.2 |
| (Physical properties) | | | | | | |
| Liquid concentration | 40% | 40% | 40% | 40% | 40% | 40% |
| Liquid/Powder ratio | 28 g/100 g | 28 g/100 g | 28 g/100 g | 28 g/100 g | 28 g/100 g | 28 g/100 g |
| Setting time (ISO) | 5'00"~10'00" | 4'00"~8'00" | 2'30"~6'00" | 4'00"~8'00" | 2'00"~6'00" | 3'00"~9'00" |
| Setting       Iso/2 hrs | — | — | — | — | — | — |
| expansion    In water/2 hrs | 11%~12% | 10%~11% | 8%~9% | 8%~9% | 6%~7% | 3%~4% |
| Compressive  ISO/1 hr | 50 Mpa | 50 Mpa | 50 Mpa | 50 Mpa | 50 Mpa | 50 Mpa |
| strength     In water/2 hrs | 30 Mpa | 30 Mpa | 30 Mpa | 30 Mpa | 30 Mpa | 30 Mpa |

TABLE 4

The difference of liquid and Liquid/Powder ratio

| (Composition) | EX 1 (Weight ratio) | EX 2 (Weight ratio) | EX 3 (Weight ratio) | EX 4 (Weight ratio) | EX 5 (Weight ratio) |
|---|---|---|---|---|---|
| α $CaSO_4$ $1/2H_2O$ | 100 | 100 | 100 | 100 | 100 |
| $CaSO_4$ $2H_2O$ | 10 | 10 | 10 | 10 | 10 |
| Surfactant: a mixture of melaminsulfonate and a formaldehyde polycondensation product | 0.2 | 0.2 | 0.2 | 0.2 | 0.2 |
| Hardening retarder: tri sodium citrate | 0.1 | 0.1 | 0.1 | 0.1 | 0.1 |
| Hardening accelerator: potassium sulfate | 0 | 0 | 0 | 0 | 0 |
| Setting expansion inhibitor: potassium tartrate | 0 | 0 | 0 | 0 | 0 |
| (Physical properties) | 0 | 0 | 0 | 0 | 0 |
| Liquid concentration | 20% | 40% | 50% | 40% | 40% |
| Liquid/Powder ratio | 28 g/100 g | 28 g/100 g | 28 g/100 g | 23 g/100 g | 45 g/1.00 g |
| Setting time (ISO) | 10'00" | 8'00" | 6'30" | 4'00" | 13'00" |
| Flow (ISO) | 38 | 33 | 29 | 25 | 60 |
| Setting expansion Iso/2 hrs | — | — | — | — | — |
| Setting expansion In water/2 hrs | 6% | 11% | 12% | 13% | 7% |
| Compressive strength ISO/1 hr | 50 Mpa | 50 Mpa | 50 Mpa | 50 Mpa | 50 Mpa |
| Compressive strength In water/2 hrs | 30 Mpa | 30 Mpa | 30 Mpa | 30 Mpa | 30 Mpa |

What is claimed is:

1. A mixture, comprising:
   a) 100 parts by weight alpha $CaSO_4 \times \tfrac{1}{2}$ $H_2O$,
   b) 1–20 parts by weight $CaSO_4 \times 2$ $H_2O$,
   c) 0.005–0.8 parts by weight of at least one additive, which is selected from the group consisting of a hardening accelerator, a hardening retarder or a setting expansion inhibitor,
   d) up to 2 parts by weight of one or two different surfactants, and
   e) 15–65 parts by weight of a colloidal silica suspension.

2. A mixture according to claim 1, wherein the $CaSO_4 \times 2$ $H_2O$ is present in amount of 2–15 parts by weight.

3. A mixture according to claim 1, wherein the hardening accelerator is selected from the group consisting of inorganic acid salts, sodium chloride, and potassium sulfate, and the hardening retarder is selected from the group consisting of carboxylates, citrates, succinates, acetates, phosphates, borates, borax, water soluble polymers, cane sugar, hexameta phosphate, etylenediamine tetra acetate, starch, gum arabic, carboxymethyl cellulose and sugar alcohol, and the setting expansion inhibitor is selected from the group consisting of potassium chloride, potassium tartrate, potassium sodium tartrate, and sodium tartrate.

4. A mixture according to claim 1, wherein the surfactants d) are selected from the group consisting of anionic surfactants, alkylbenzene sulfonates, alkylnaphthalene sulfonates, a mixture of naphthalene sulfonates and formaldehyde polycondensation products, a mixture of melamin sulfonates and formaldehyde polycondensation products, dialkylsulfosuccinates, alkylsulfoacetates, alpha-olefin sulfonates, sodium N-acyl methyl taurates, nonionic surfactants, polyethylene alkylethers, polyoxyethylene sec-alcoholethers, polyethylene polyoxypropylene alkylethers, and polyglyceryl fatty acid esters.

5. A mixture according to claim 1, wherein the colloidal silica suspension (e) has a concentration of 20–50 wt.-%.

6. A die produced by molding the mixture of claim 1.

7. A kit containing the following components:
   a) 100 part by weight alpha $CaSO_4 \times \tfrac{1}{2}$ $H_2O$,
   b) 1–20 parts by weight $CaSO_4 \times 2$ $H_2O$,
   c) 0.005–0.8 part weight of at least one additive, which is selected from the group consisting of hardening accelerator, a hardening retarder or setting expansion inhibitor,
   d) up to 2 part by weight of one or two different sufactants, and
   e) 15–65 part by weight of a colloidal silica suspension, wherein each component is provided in separate containers.

8. A die produced by mixing and molding the components of the kit of claim 7.

* * * * *